United States Patent
Shelton, IV

(10) Patent No.: US 7,147,138 B2
(45) Date of Patent: Dec. 12, 2006

(54) SURGICAL STAPLING INSTRUMENT HAVING AN ELECTROACTIVE POLYMER ACTUATED BUTTRESS DEPLOYMENT MECHANISM

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/181,471

(22) Filed: Jul. 14, 2005

(65) Prior Publication Data

US 2006/0025816 A1    Feb. 2, 2006

Related U.S. Application Data

(60) Provisional application No. 60/591,694, filed on Jul. 28, 2004.

(51) Int. Cl.
*A61B 17/00* (2006.01)

(52) U.S. Cl. .................. 227/176.1; 227/19; 227/177.1; 227/181.1

(58) Field of Classification Search ............... 227/19, 227/176.1, 177.1, 181.1; 606/139, 148, 151
See application file for complete search history.

(56) References Cited

U.S. PATENT DOCUMENTS

| | | | |
|---|---|---|---|
| 5,263,629 A * | 11/1993 | Trumbull et al. | 227/181.1 |
| 5,397,324 A * | 3/1995 | Carroll et al. | 606/139 |
| 5,441,193 A | 8/1995 | Gravener | |
| 5,465,895 A | 11/1995 | Knodel et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,673,840 A | 10/1997 | Schulze et al. | |
| 5,673,841 A | 10/1997 | Schulze et al. | |
| 5,702,409 A | 12/1997 | Rayburn et al. | |
| 5,769,892 A | 6/1998 | Kingwell | |
| 5,797,537 A | 8/1998 | Oberlin et al. | |
| 5,810,855 A | 9/1998 | Rayburn et al. | |
| 5,865,361 A | 2/1999 | Milliman et al. | |
| 5,902,312 A | 5/1999 | Frater et al. | |
| 5,908,427 A | 6/1999 | McKean et al. | |
| 5,964,774 A | 10/1999 | McKean et al. | |
| 6,063,097 A | 5/2000 | Oi et al. | |
| 6,503,257 B1 | 1/2003 | Grant et al. | |
| 6,656,193 B1 | 12/2003 | Grant et al. | |

(Continued)

FOREIGN PATENT DOCUMENTS

EP        0 832 605        4/1998

(Continued)

OTHER PUBLICATIONS

EPO Search Report, Application No. 05254680.1, Jan. 12, 2006, pp. 1-5.

(Continued)

*Primary Examiner*—John Sipos
*Assistant Examiner*—Michelle Lopez

(57) ABSTRACT

A surgical instrument for being endoscopically or laparoscopically inserted to a surgical site for simultaneous stapling and severing of tissue includes electrically actuated deployment of buttress pads held on inner surfaces of upper and lower jaws of a staple applying assembly. Thereby, thick or thin layers may be stapled and severed without improper staple formation nor with nonoptimal deployment of the buttress pads. Electroactive polymer (EAP) actuated latches, an EAP channel, or a rigid channel with an EAP pinch lock reliably hold the buttress pad until deployment is desired with a low force to separate the stapled and severed buttress pad/tissue combination with the respective EAP mechanism activated for deployment.

20 Claims, 16 Drawing Sheets

U.S. PATENT DOCUMENTS

| | | |
|---|---|---|
| 6,667,825 B1 | 12/2003 | Lu et al. |
| 6,835,173 B1 | 12/2004 | Couvillon, Jr. |
| 2003/0065358 A1 | 4/2003 | Frecher |
| 2003/0069474 A1 | 4/2003 | Couvillion et al. |
| 2004/0232196 A1 | 11/2004 | Shelton et al. |
| 2004/0232197 A1 | 11/2004 | Shelton et al. |
| 2005/0006434 A1 | 1/2005 | Wales et al. |
| 2005/0067457 A1 | 3/2005 | Shelton et al. |
| 2005/0067458 A1 | 3/2005 | Swayze et al. |
| 2005/0173490 A1 | 8/2005 | Shelton |

FOREIGN PATENT DOCUMENTS

| | | |
|---|---|---|
| EP | 1 522 264 | 4/2005 |
| WO | WO 99/02090 | 1/1999 |
| WO | WO 03/094743 | 11/2003 |
| WO | WO 2004/050971 | 6/2004 |

OTHER PUBLICATIONS

EPO Search Report, Application No. 05254694.2, Jan. 12, 2006, pp. 1-5.

EPO Search Report, Application No. 05254685.0, Jan. 12, 2006, pp. 1-5.

EPO Search Report, Application No. 05254695.9, Jan. 12, 2006, pp. 1-5.

EPO Search Report, Application No. 05254685.0, Jan. 12, 2006.

* cited by examiner

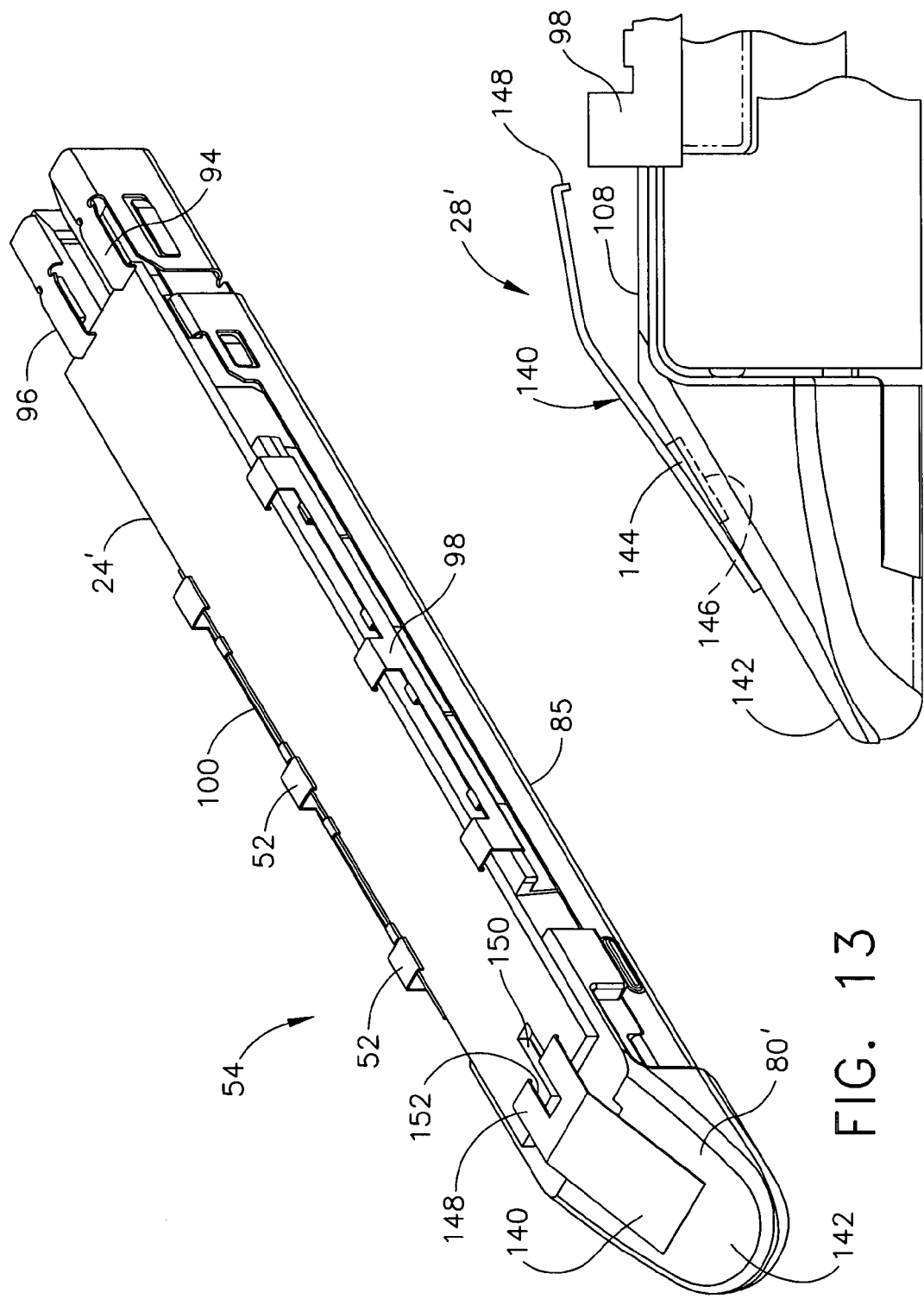

SURGICAL STAPLING INSTRUMENT HAVING AN ELECTROACTIVE POLYMER ACTUATED BUTTRESS DEPLOYMENT MECHANISM

CROSS REFERENCE TO RELATED APPLICATIONS

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments including adding bolstering material to the severed and stapled tissue.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from the proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

One known problem with using surgical staplers in this fashion has been the formation of air leaks in stapled lung tissue. The leaks can occur in the cut line, and/or in the staple holes themselves. Frequently, the diseased lung tissue is thin and friable and can tear at the staples as the lungs re-inflate. These air leaks can be persistent and can extend the hospital stay for a patient by weeks. To alleviate these leakage problems, surgeons reinforce the staple line by applying a buttress or pledget material to the desired stapling site and stapling through the buttress material. The buttress material provides reinforcement to the friable tissue. The tissue is compressed against the staple holes resulting in increased pneumostasis. This reduces the chances of tissue tearing at the staple line, and reduces staple pullout in friable tissue.

These reinforcement materials are typically releasably mounted onto the jaw members of a surgical stapling device such that upon firing, the reinforcement material is stapled to the lung tissue. Optimally the lung tissue is "sandwiched" between two layers of this reinforcement material. Alternately, buttress materials can be used in a number of other surgical procedures such as but not limited to: an ovarian hysterectomy, a gastric bypass, an anastomosis of intestinal tissue, or any other procedure that requires reinforcement of a staple line or increased hemostasis in tissue.

Releasably attaching the buttress material to the jaw members of the surgical stapling device presents a special challenge. The buttress material must be fastened securely to the jaws of the surgical stapling device so that it will not fall off during normal operation, yet the material must be easily released from the surgical stapling device after the staples are fired. A variety of adhesive and mechanical attachment means are known. Both adhesive and mechanical attachment means are discussed below, and both have their deficiencies.

One example of a device which attaches a buttress material to a linear cutter with an adhesive is described in U.S. Pat. No. 5,441,193 by Gravener et al. This device attaches buttress materials to a surgical instrument with a biocompatible cyanoacrylate adhesive. The adhesive bonding is applied along the edge portions of the buttress material and dashed lines of perforations are placed within the buttress material (adjacent to the glue line) so that the unglued central portion of the buttress material can be torn from the glued edge portions. However, the portions of the buttress material having the adhesive applied thereto are not releasable from the device. As a consequence, removing the buttress from the instrument (after firing) can be especially difficult, as all of the material between the perforations must be torn simultaneously to release the surgical stapling device from tissue. An improved approach to adhesively engaged buttress material was subsequently disclosed in U.S. Pat. No. 6,656,193 to Grant that included both mechanical alignment features in combination with a reliable adhesive with beneficial characteristics for attachment and detachment.

It is also known to employ various mechanical attachments of the buttress material to the surgical stapling and severing instrument. Many methods of mechanical attachment exist, and a common one is the placement of a sleeve over the clamping members of the surgical stapling device. The sleeves can be formed from flexible fabric such as buttress material, or can contain a releasable strip of buttress material attached to a different fabric. Many of these sleeves are described in U.S. Pat. Nos. 5,503,638 and 5,549,628 by Cooper et al, in U.S. Pat. No. 5,702,409 by Rayburn et al., in U.S. Pat. No. 5,810,855 by Rayburn et al., and in U.S. Pat. No. 5,964,774 by McKean et al.

While sleeves can effectively be used to attach the buttress material to the end effector of the surgical stapling device, sleeves can cause other complications during surgery. For example, if the sleeve is formed from a solid sleeve of buttress material, such as in U.S. Pat. Nos. 5,902,312 and 5,769,892, firing the surgical stapling device staples the buttress and tissue and severs the buttress sleeve and tissue between the staple lines. This action leaves the portions of tissue (on either side of the cut line) attached together by a sheet of buttress material. This requires the surgeon to go in and sever the cut sleeve of the buttress to separate the severed tissue, and remove any unwanted portion of the buttress material.

It is also known to incorporate frangible features that are a compromise between a strong hold to prevent inadvertent detachment and unduly high force to detach after stapling. For instance, in U.S. Pat. Nos. 5,542,594, 5,908,427, and 5,964,774 to McKean et al., buttress material is pinned onto end effector surfaces. In U.S. Pat. Nos. 5,702,409 and 5,810,855 to Rayburn et al., porous polytetrafluoroethylene (PTFE) tubes fit over each jaw with each having a tear away flat face. As a compromise, it would be desirable that retention force be higher prior to stapling and reduced after stapling.

Consequently, a significant need exists for an improved surgical stapling and severing instrument that may reliability position buttress material on each side of tissue that is to be stapled and severed with the buttress material thereafter easily deployed from the instrument.

BRIEF SUMMARY OF THE INVENTION

The invention overcomes the above-noted and other deficiencies of the prior art by providing a surgical instrument that reliably engages buttress material to a tissue compression surface of a fastener applying assembly by use of an electrically actuated retention member. Thereby, a strong engagement avoids inadvertent deployment yet the electrically actuated retention member may be switched to a disengaged state to effect deployment of the buttress material after fastening to tissue without need for subsequent surgical procedures.

In one aspect of the invention, a surgical instrument for fastening buttress material to tissue has a staple applying assembly distally attached to an elongate shaft that responds to distal motion of a firing member to form staples between opposing tissue compression surfaces through first and second buttress pads and interposed compressed tissue. Electrically actuated retention members selectively positioned between an engaged position holding a selected buttress pad to a selected tissue compression surface are controlled by circuitry to effect a selected one of retaining and deploying the buttress pad. Thereby, reliance of a static amount of retention force is replaced by a selectable amount of force.

In another aspect of the invention, a surgical instrument for fastening buttress material to tissue incorporates the advantages of electroactive polymers to serve as a means for engaging a buttress pad to each of a pair of tissue compression surfaces and to remotely electrically control deployment of the buttress pads after their stapling to interposed tissue. Thereby, an implement portion of such a surgical instrument may be desirably small in transverse cross section for insertion through a cannula of a trocar for endoscopic or laparoscopic procedures.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 13 is a front left perspective view of a replaceable staple cartridge removed from the lower jaw of the alternative staple applying assembly of FIG. 12.

FIG. 14 is a left side detail view of the lower jaw of FIG. 12 with the lower, front EAP latch activated to disengage from an omitted deployed buttress pad.

DETAILED DESCRIPTION OF THE INVENTION

Figure 1:
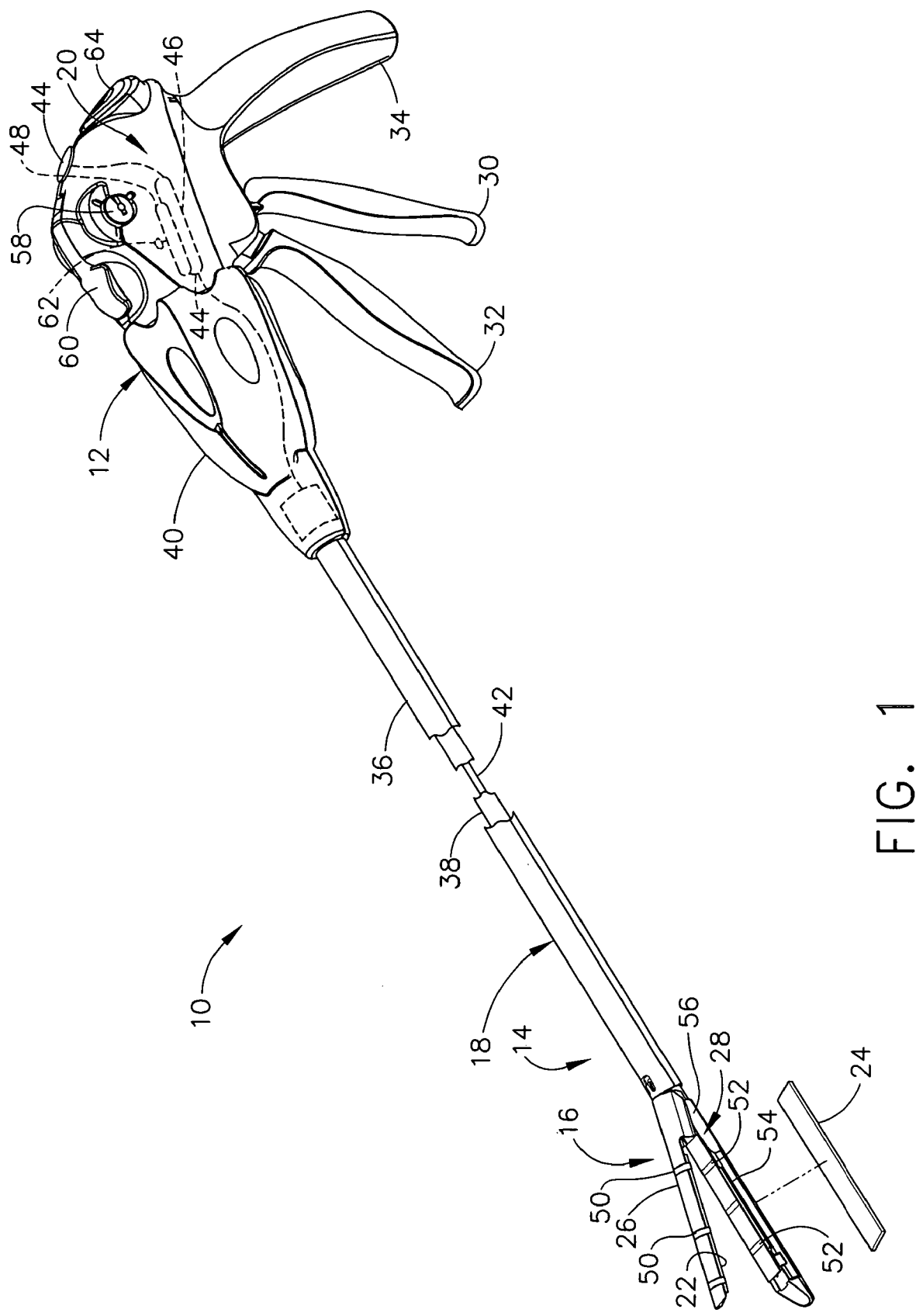
FIG. 1 depicts a partially cutaway side elevation view of a surgical stapling and severing instrument in an open position with an electrically actuated buttress deployment mechanism with a lower buttress pad exploded off a lower jaw and an elongate shaft partially cut away.
Figure 2:
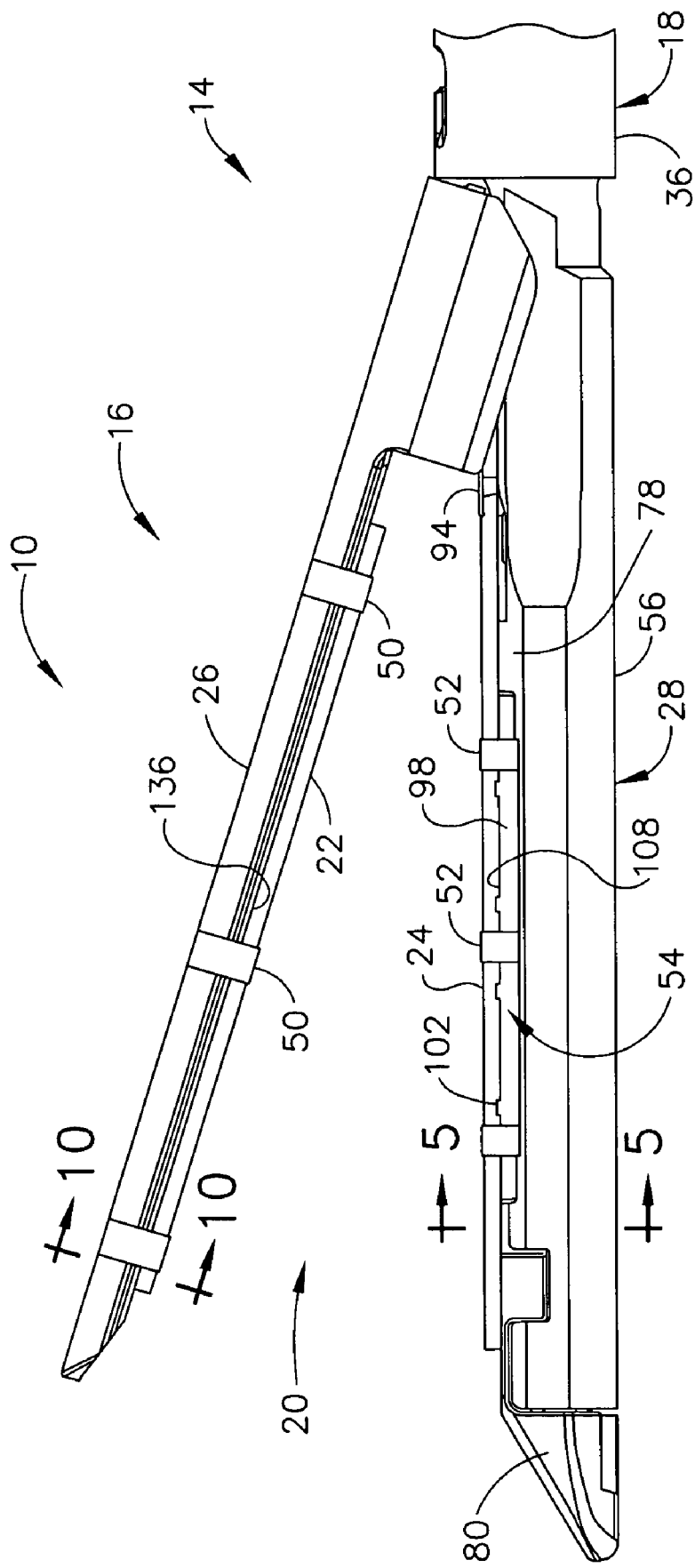
FIG. 2 depicts a left side view in elevation of a staple applying assembly of the surgical stapling and severing instrument of FIG. 1.

Turning to the Drawings, wherein like numerals denote like components throughout the several views, in FIGS. 1–2, a surgical stapling and severing instrument 10 includes a handle portion 12 that manipulates to position an implement portion 14 formed from a fastening end effector, specifically a staple applying assembly 16, distally attached to an elongate shaft 18. The implement portion 14 is sized for insertion through a cannula of a trocar (not shown) for an endoscopic or laparoscopic surgical procedure. Advantageously, an electrically actuated buttress deployment mechanism 20 reliability retains upper and lower buttress pads 22, 24 respectively on an upper jaw (anvil) 26 and a lower jaw 28 until tissue clamped within the staple applying assembly 16 is stapled and severed. Thereafter, the electrically actuated buttress deployment mechanism 20 deploys the buttress pads 22, 24 without undue force or ancillary surgical procedures (e.g., use of a grasper).

The surgical stapling and severing instrument 10 is in an initial state as depicted in FIG. 1, with a closure trigger 30 and a more distal firing trigger 32 both released from a pistol grip 34. Release of the closure trigger 30 proximally draws a closure sleeve 36, which is an outer portion of the elongate shaft 18 that pivots the anvil 26. The lower jaw 28 is supported by a frame ground 38 that is encompassed by the closure sleeve 36 and is rotatably engaged to the handle portion 12. A rotation knob 40 allows reciprocating longitudinal motion of the closure sleeve 36 while engaging the closure sleeve 36 and frame ground 38 for rotation about a longitudinal axis of the elongate shaft 18. The firing trigger 32 is either directly or intermittently coupled to a firing member, specifically a firing rod 42, guided by the frame ground 38 that transfers a firing motion to the staple applying assembly 16 to effect stapling and severing.

A power button 44 may be depressed by the user to activate a control module 46 of the electrically actuated buttress deployment mechanism 20, powered by a battery 48. A visual confirmation on the handle portion 12 may be given to the user as to the state of the electrically actuated buttress deployment mechanism 20 (e.g., color/flash illumination of the power button 44). For instance, the power button 44 and/or other user interfaces (not shown) may advantageously be depressed a number of times to toggle through several available operational states of the electrically actuated buttress deployment mechanism 20, such as "POWER ON", "BUILT-IN TEST PASSED", INSERT BUTTRESS PADS, "SYSTEM LOADED/AWAITING FIRING", "FAULT DETECTED", and "BUTTRESS OVERRIDE/FIRING WITHOUT INSTALLED BUTTRESS PADS". Additional programming flexibility may be achieved by incorporating a wired or wireless (e.g., BLUETOOTH) protocol to interface the control module 46 to an external graphical user interface (e.g., personal computer). In the initial state, the control module 46 electrically actuated buttress retention elements, in the version depicted, comprise upper and lower latch arms 50, 52 that are electrically urged outwardly so that the upper buttress pad 22 may be inserted against an inner surface of the anvil 26 as depicted and a lower buttress pad 24 may be placed upon and latched to an inner surface of the lower jaw 28, in particular, upon a replaceable staple cartridge 54 that is engaged in an elongate staple channel 56 of the lower jaw 28.

With the buttress pads 22, 24 inserted and the power button 44 depressed again to latch, the implement portion 14 may be inserted endoscopically or laparoscopically to a surgical site. The closure trigger 30 is depressed and released as necessary until an amount of tissue is gripped in the staple applying assembly 16. Drawing the closure trigger 30 fully to the pistol grip 34 causes the closure trigger 30, and thus the anvil 26, to clamp in a closed position. Then, the firing trigger 32 is depressed, either in a single stroke or in a series of strokes depending upon the configuration of the handle portion 12 causing full firing travel of the firing rod 42. For multiple firing strokes, a firing indicator wheel 58 on the handle portion 12 gives a visual indication as to the amount of firing that has occurred. It should be appreciated that a distal end of the firing rod 42 includes or is coupled to a knife that traverses a vertical slot in the staple cartridge 54 to sever clamped tissue and the buttress pads 22, 24. The firing rod is also coupled to a wedge assembly that cams staples upwardly out of the staple cartridge 54 through the clamped tissue and buttress pads 22, 24 to close and form against the anvil 26. Thereafter, the firing rod 42 is withdrawn by an end-of-firing travel release mechanism and a retraction bias in the handle portion 12. For manually releasing and/or manually retracting the firing rod 42, a manual retraction lever 60 may be rotated upwardly on the handle portion 12. The control module 46 of the electrically actuated buttress deployment mechanism 20 advantageously senses that firing has been accomplished, such as by being responsive to a firing position sensor 62 in the handle portion 12. With the unclamping of the closure trigger 30 by depressing a closure release button 64, the severed ends of buttressed, stapled tissue (not shown) is released from the staple applying assembly 16.

An illustrative version of the handle portion 12 without an electrically actuated buttress deployment mechanism 20 is described in U.S. patent application Ser. No. 11/052,387 entitled "SURGICAL STAPLING INSTRUMENT INCORPORATING A MULTI-STROKE FIRING MECHANISM WITH RETURN SPRING ROTARY MANUAL RETRACTION SYSTEM" to Shelton et al., the disclosure of which is hereby incorporated by reference in its entirety.

ELECTROACTIVE POLYMERS

While a number of electrical actuators (e.g., solenoids) may be integrated into the staple applying assembly 16, illustrative versions described herein advantageously employ electroactive polymers (EAP), which are conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types of EAPs and multiple configurations of each type. The two basic types are a fiber bundle and a laminate version. The fiber bundle consists of fibers around 30–50 microns. These fibers may be woven into a bundle much like textiles and are often called EAP yarn because of this. This type of EAP contracts when voltage is applied. The electrodes are usually made up of a central wire core and a conductive outer sheath that also serves to contain the ionic fluid that surrounds the fiber bundles. An example of a commercially available fiber EAP material, manufactured by Santa Fe Science and Technology and sold as PANION™ fiber, is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is from Artificial Muscle Inc, a division of SRI Laboratories. Plate EAP material is also available from EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. The laminate version may also be adhered to either side of a flexible plate. When one side of the flexible plate EAP is energized, it expands flexing the plate in the opposite direction. This allows the plate to be flexed in either direction, depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2–4% where the typical laminate version achieves 20–30%, utilizing much higher voltages.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers therebetween to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Figure 3:
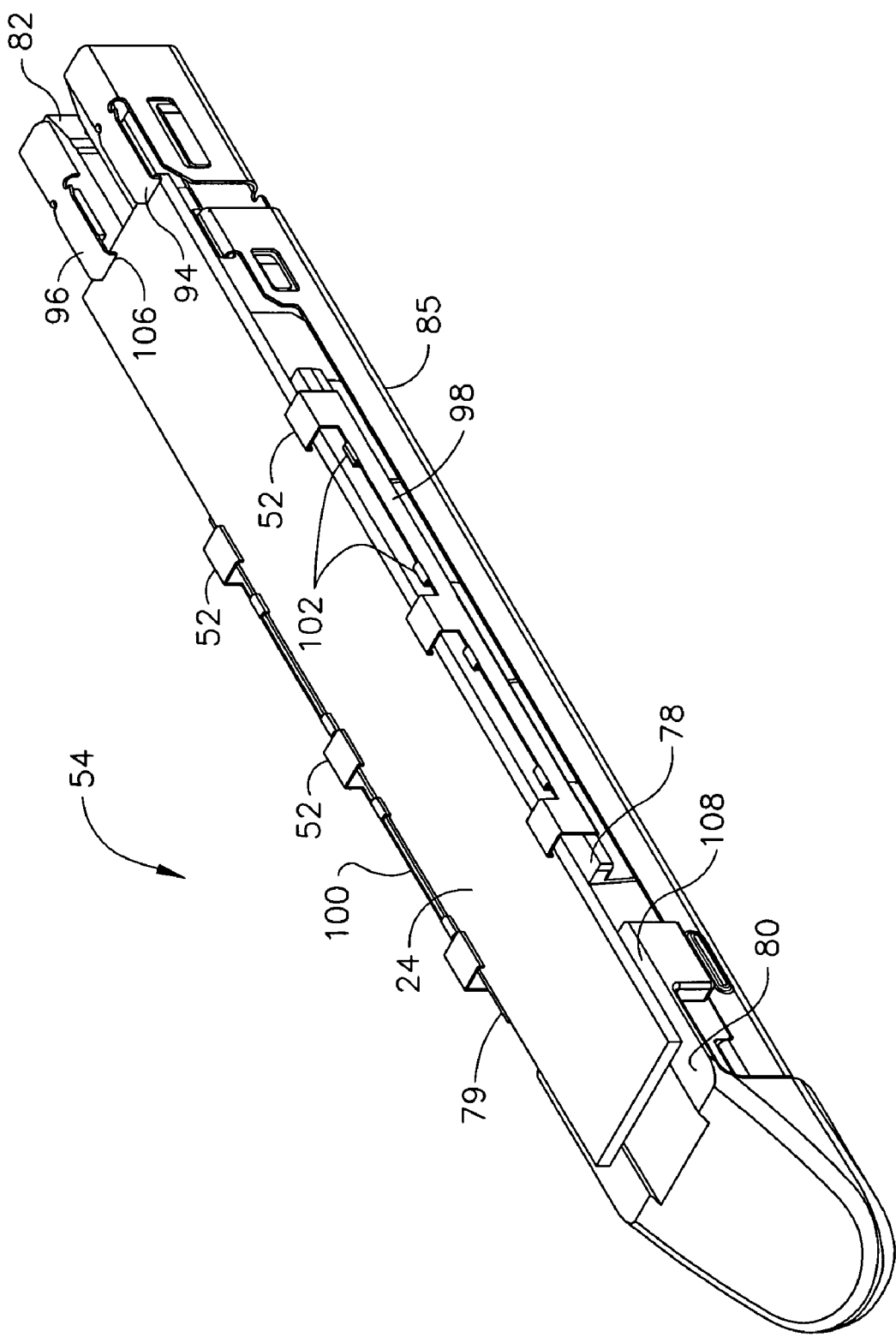
FIG. 3 depicts a left front perspective view of a replaceable staple cartridge removed from the lower jaw of the staple applying assembly of FIG. 2.
Figure 4:
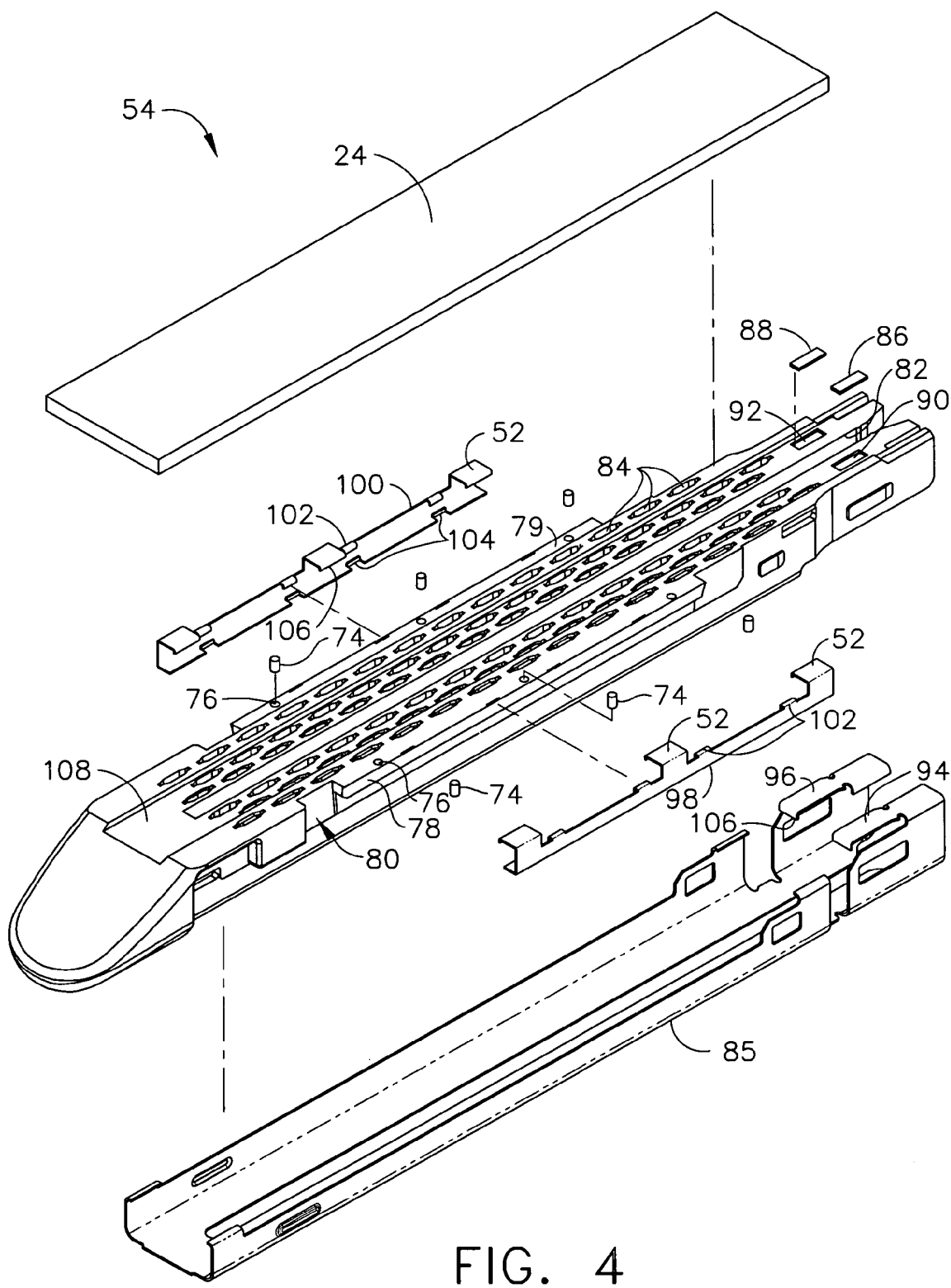
FIG. 4 is a left front perspective disassembled view of the replaceable staple cartridge of FIG. 3.
Figure 5:
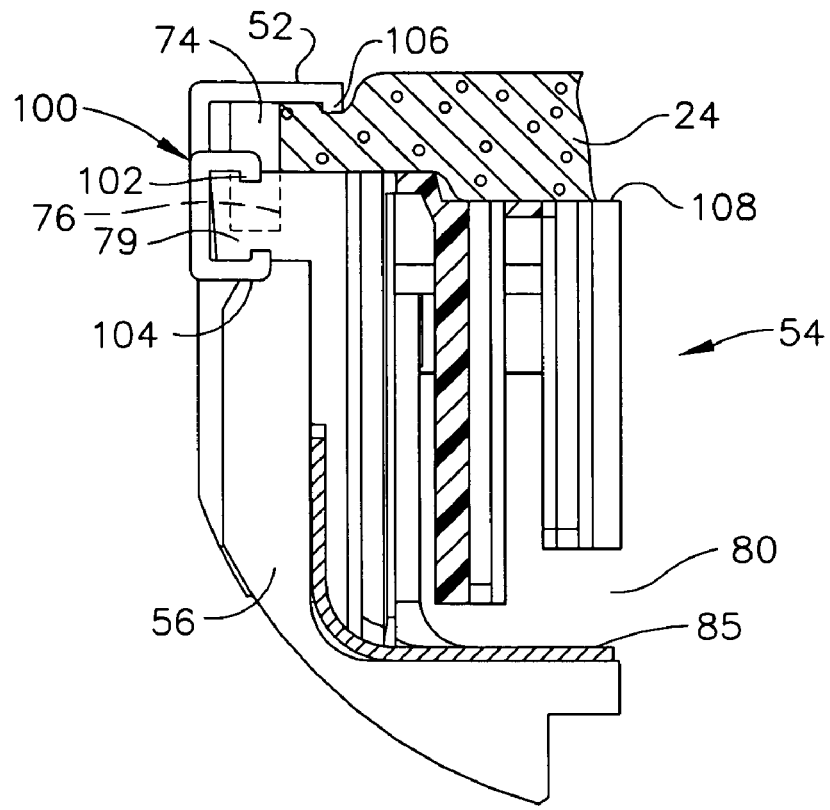
FIG. 5 is a front view of a right side of the lower jaw taken in cross section along lines 5—5 of FIG. 2 with a lower, lateral electroactive polymer (EAP) buttress latch in a locked state.
Figure 6:
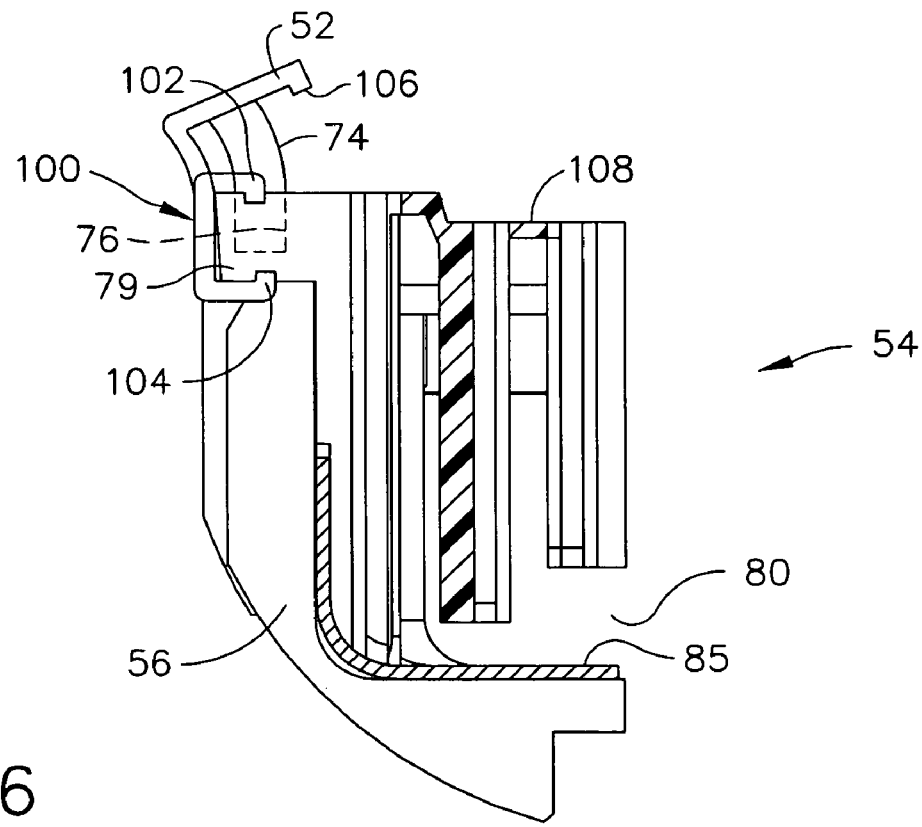
FIG. 6 is a front view of the right side of the lower jaw taken in cross section along lines 5—5 of FIG. 2 with the lower, lateral EAP buttress latch in an unlocked state.
Figure 7:
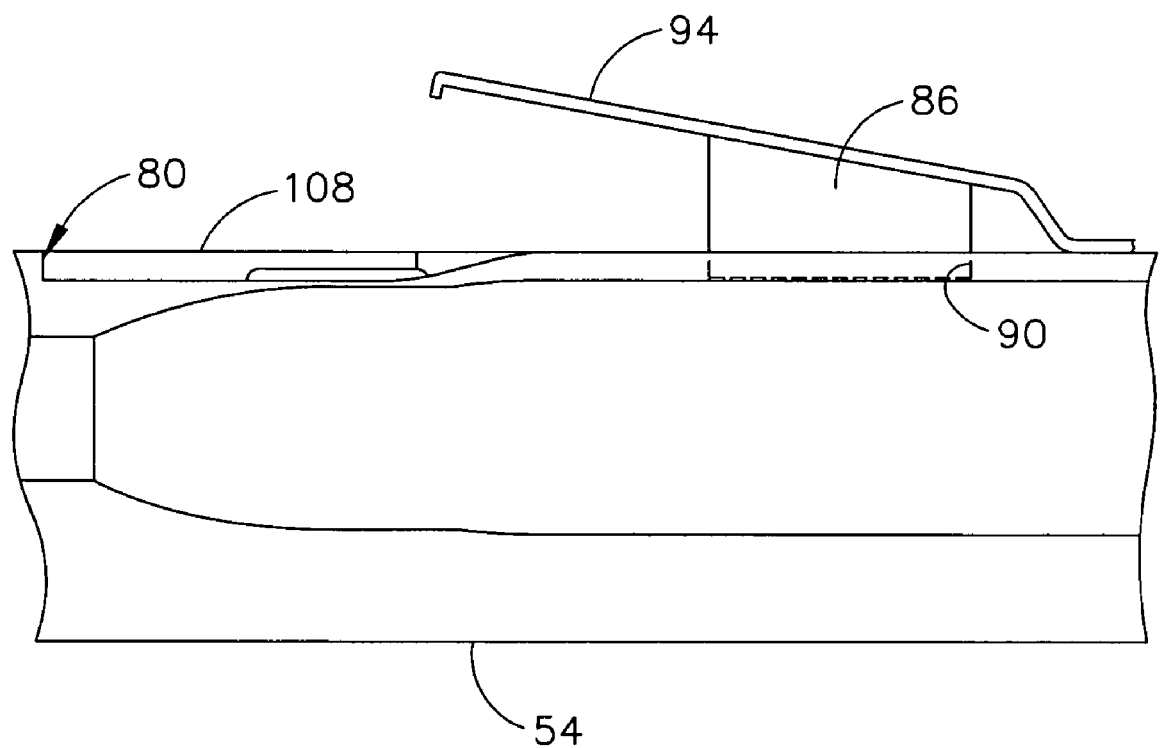
FIG. 7 is a left side detail view of an aft EAP buttress latch in an unlocked state.
Figure 8:
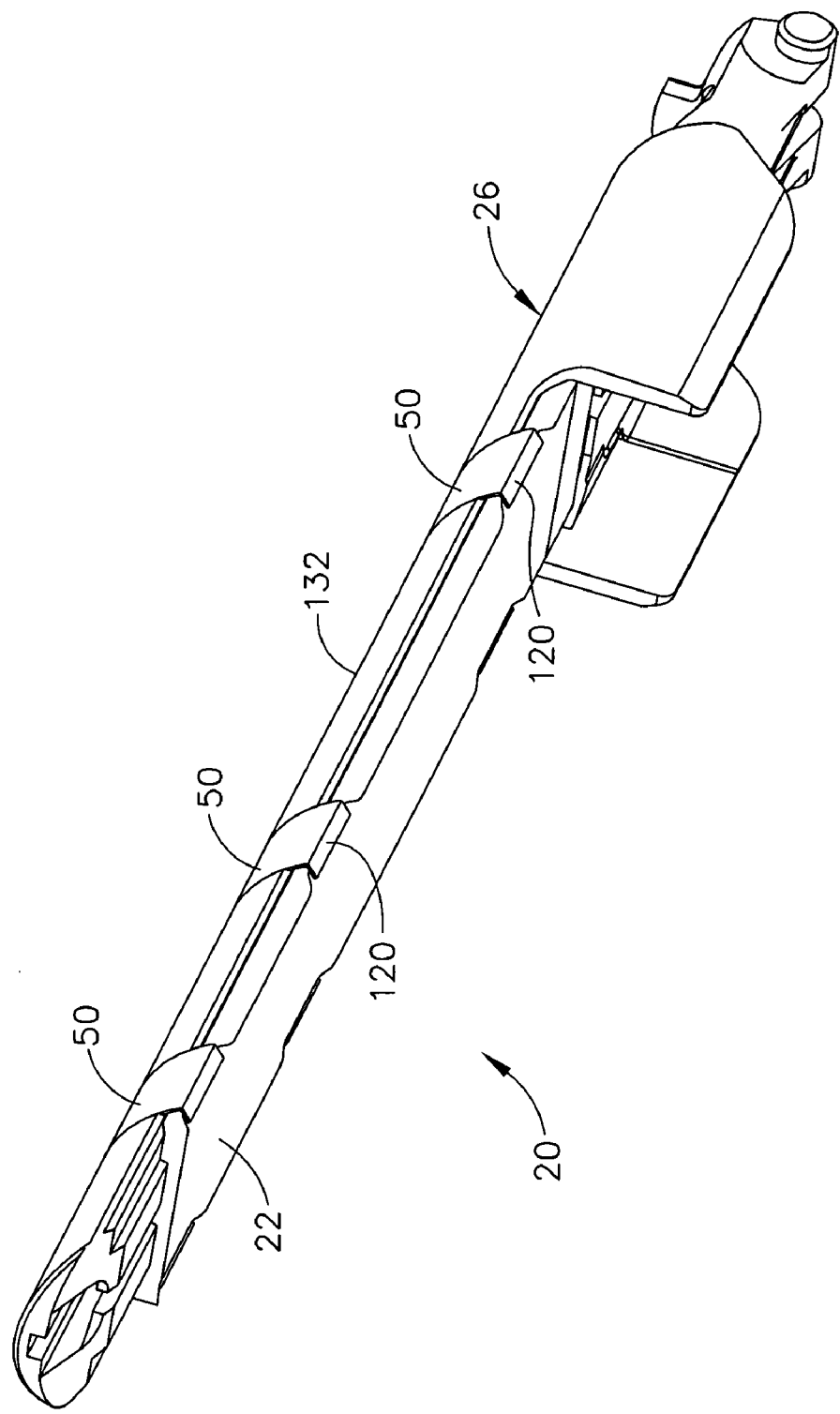
FIG. 8 is a left perspective view of an upper jaw (anvil) of the staple applying assembly of FIG. 2.
Figure 9:
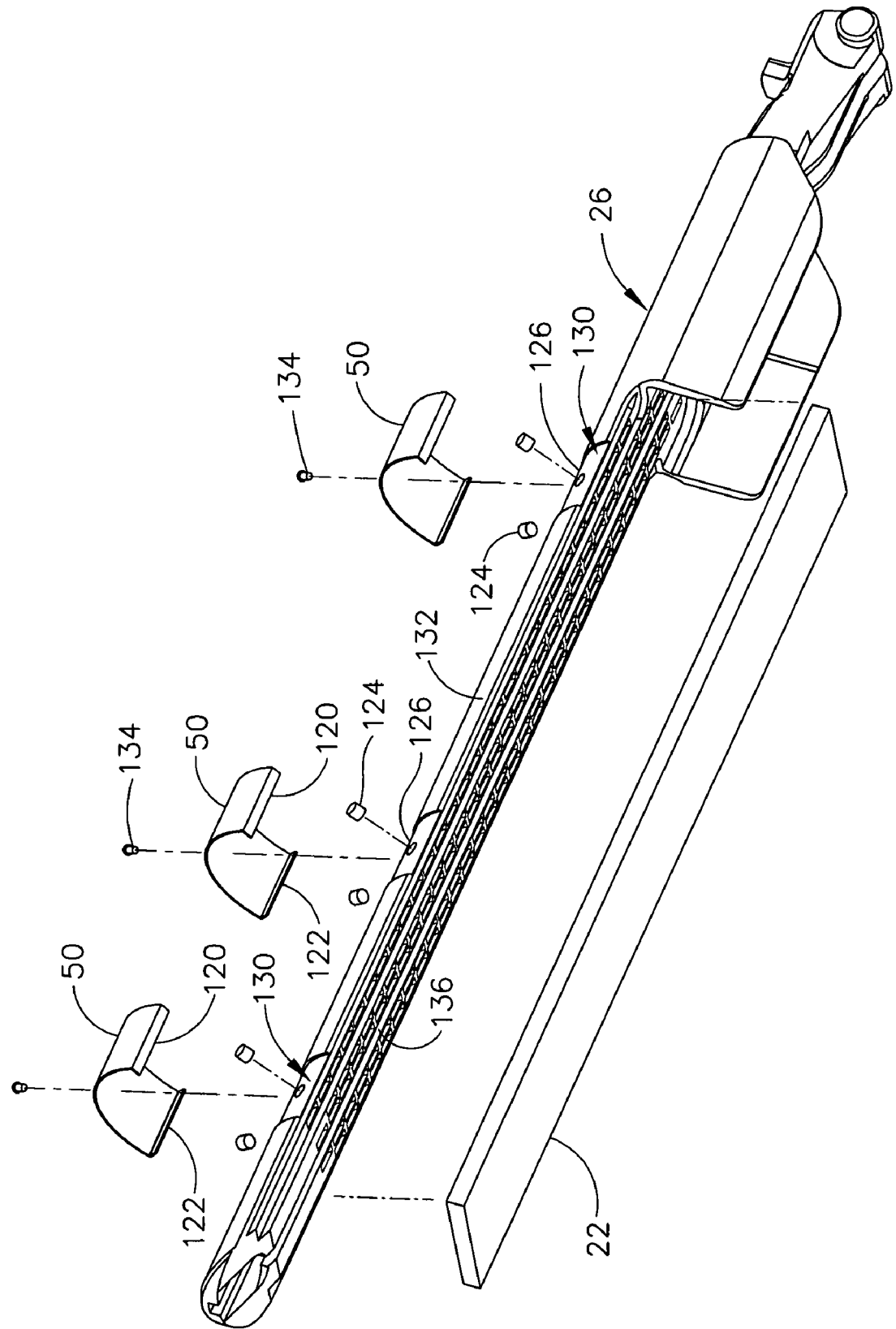
FIG. 9 is a left perspective, disassembled view of the upper jaw (anvil) of the staple applying assembly of FIG. 2.
Figure 10:
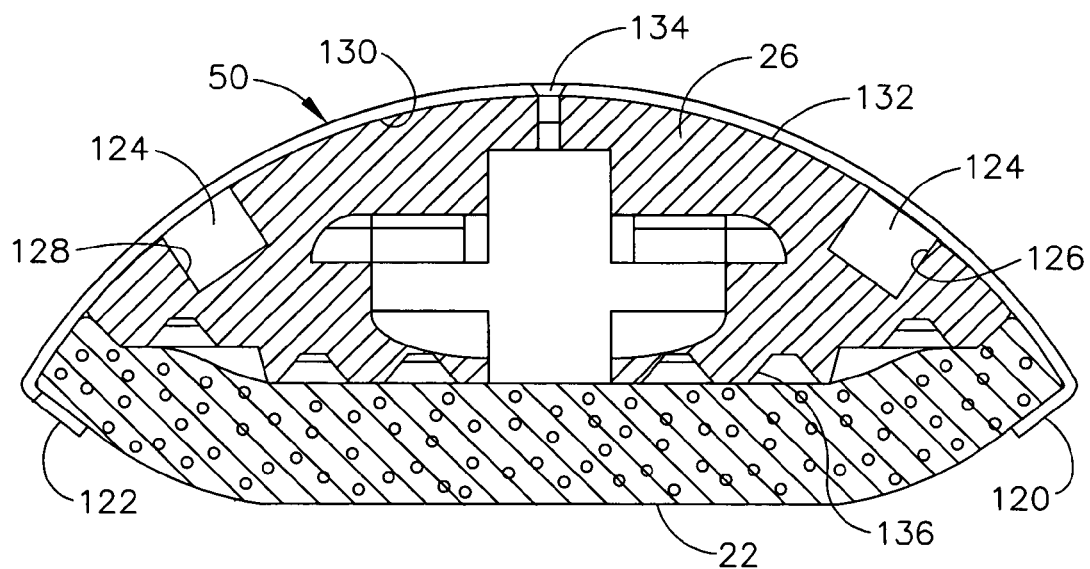
FIG. 10 is a front view of the upper jaw (anvil) of the staple applying assembly of FIG. 2 taken in cross section through lines 10—10 with an upper, lateral EAP latch engaged to a buttress pad.

In FIGS. 3–7, the lower latch arms 52 of the electrically actuated buttress deployment mechanism 20 selectively hold the lower buttress pad 24 by electrically actuating cylindrical EAP actuators 74 positioned in holes 76 formed in left and right lateral lips 78, 79 of a staple cartridge body 80 of the replaceable staple cartridge 54. With particular reference to FIG. 4, the polymeric staple body 80 has an aft vertical slot 82 that receives a knife of a firing bar (not shown). A plurality of vertical staple apertures 84 are formed in the polymeric staple body 80 with each containing a staple supported by staple drivers (not shown). A staple cartridge tray 85 underlies and laterally encompasses the polymeric staple body 80 to retain these components. Left and right aft rectangular EAP actuators 86, 88 extend out of left and right aft rectangular apertures 90, 92 formed in the staple cartridge body 80 on each side of the aft vertical slot 82. Left and right aft latch arms 94, 96 are formed into the staple cartridge tray 85 attached at their aft portion and horizontally extending distally to bend front upwardly as the respective aft rectangular EAP actuators 86, 88 expand (FIG. 7). Separate left and right side brackets 98, 100 each include a plurality of opposing and inwardly bent top and bottom flanges 102, 104 that grip respective left and right lateral lips 78, 79. The lower latch arms 52 are formed from the left and right side brackets 98, 100 as L-shaped flanges that overlie and are spaced away from the respective left and right lateral lips 78, 79. Each side latch arm 52 and aft latch arm 94, 96 has a down turned inward edge 106 that assists in gripping the lower buttress pad 24 (FIGS. 3, 5). In FIG. 6, electrical activation of cylindrical EAP actuators 74 rotates the lower latch arms 52 upwardly and laterally allowing the lower buttress pad 24 to deploy away from a top compression surface 108 of the replaceable staple cartridge 54.

Figure 11:
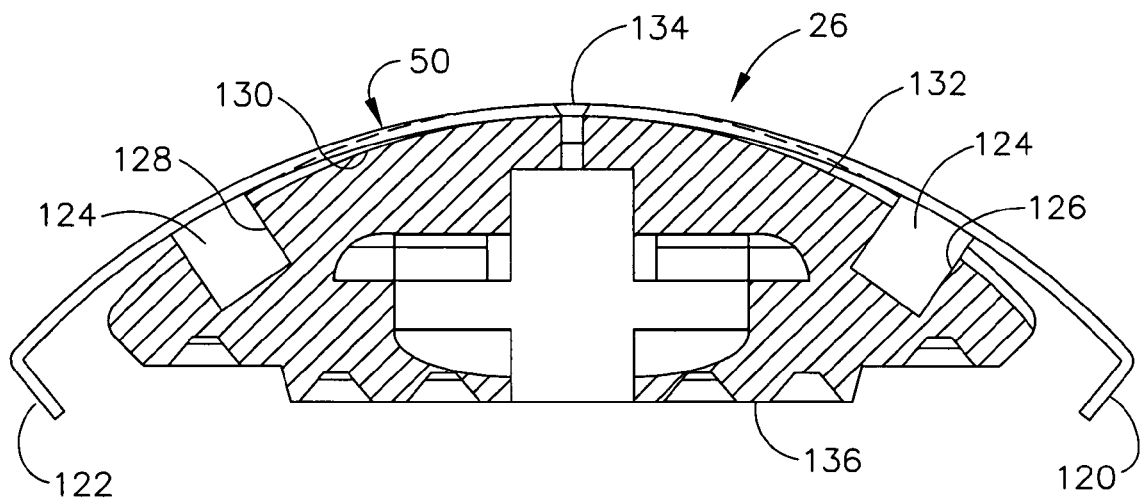
FIG. 11 is a front view of the upper jaw (anvil) of the staple applying assembly of FIG. 2 taken in cross section through lines 10—10 with the upper lateral EAP latch actuated and the deployed buttress pad omitted.
Figure 12:
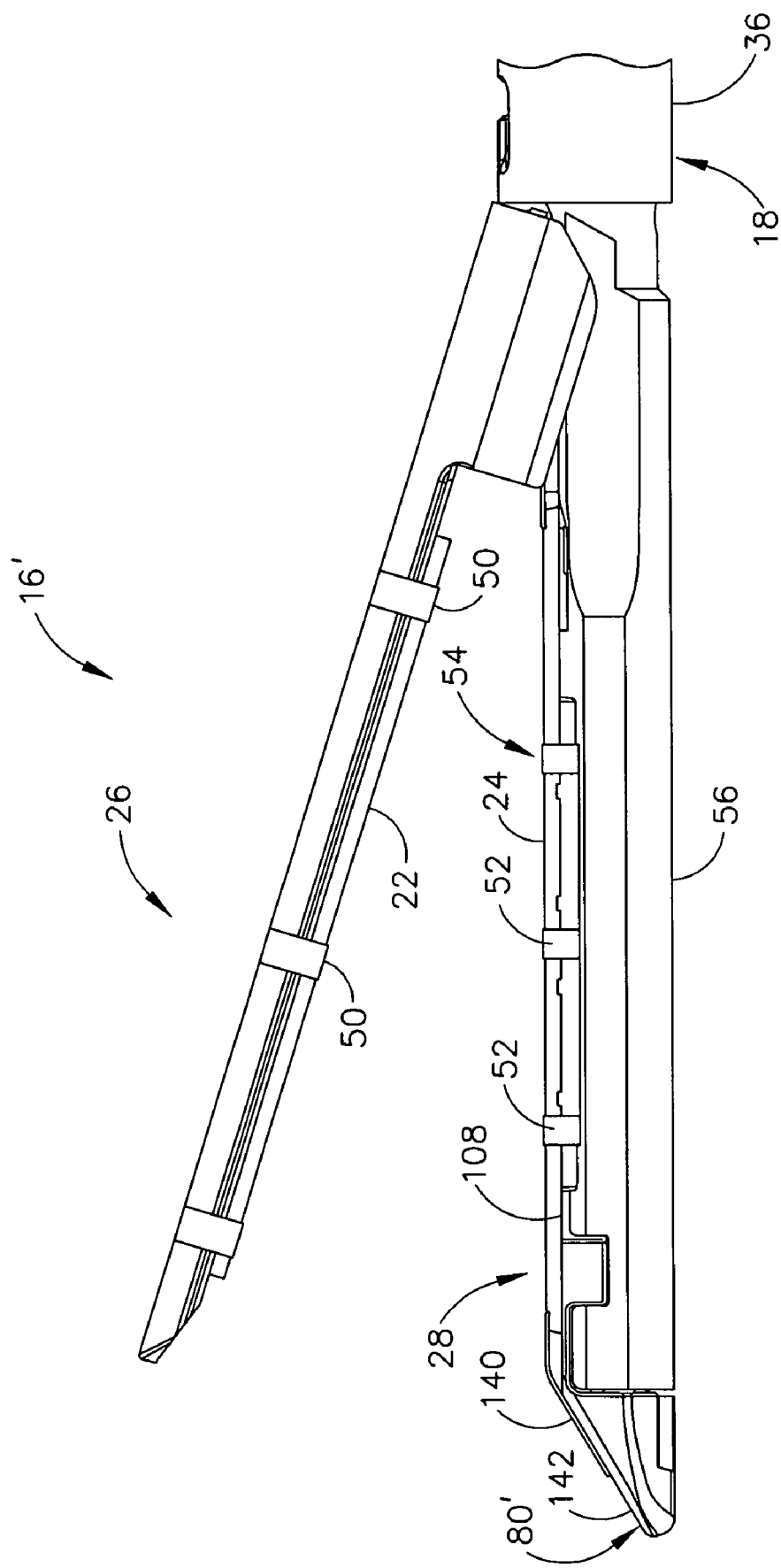
FIG. 12 is a left side view in elevation of an alternative staple applying assembly for the surgical stapling and severing instrument of FIG. 1 with a lower, front EAP latch engaged to a lower buttress pad.
Figure 15:
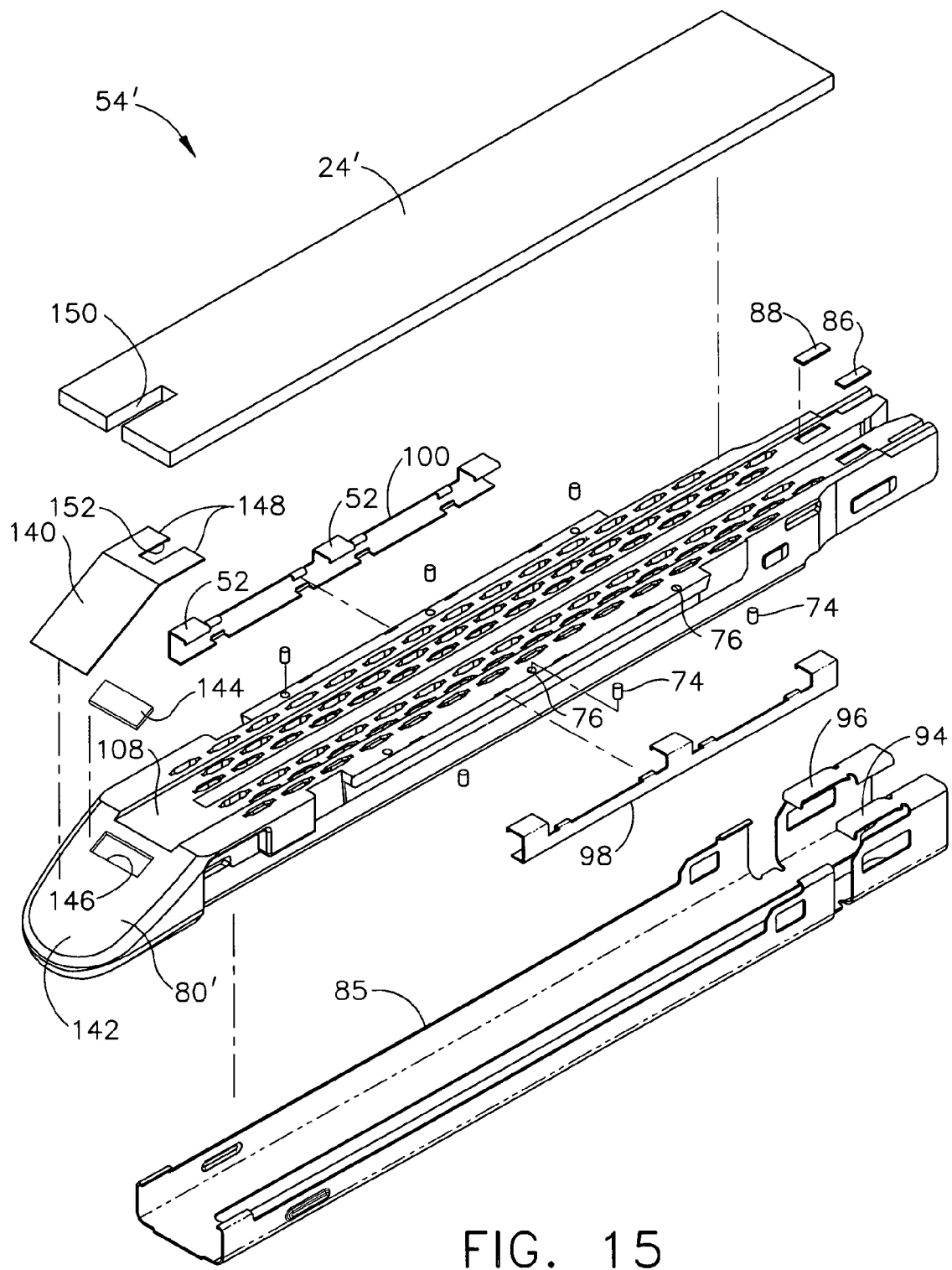
FIG. 15 is a left perspective disassembled view of the lower jaw of FIG. 12 with a slotted buttress pad.

In FIGS. 8–11, the upper latch arms 50 of the electrically actuated buttress deployment mechanism 20 are curved to closely overlay the anvil 26 with inwardly curved left and right tips 120, 122 that parallel a respective outer edge of the anvil 26. Each upper latch arm 50 is electrically actuated by a pair of cylindrical EAP actuators 124 that extend out of a respective left and right holes 126, 128 formed into arm recess 130 that is formed laterally across a top surface 132 of the anvil 26. At a longitudinal apex of the anvil 26, each upper latch arm 50 is fastened to the anvil 26 by a fastener 134. Thus expansion of the pair of cylindrical EAP actuators 124 on each side of the respective fastener 134 causes the left and right tips 120, 122 of each upper latch arm 50 to raise and rotate away from the retained upper buttress pad 22 allowing deployment from a staple forming inner compression surface 136 of the anvil 26 (FIG. 11).

In FIGS. 12–15, a version of a replaceable staple cartridge 54' of a lower jaw 28' of a staple applying assembly 16' as otherwise described in FIGS. 3–6 further includes a lower distal latch 140 that is a plate bent into an obtuse angle corresponding to a beveled lead edge 142 and the top compression surface 108 of a staple cartridge body 80'. A lower distal EAP actuator 144 extends out of a distal EAP recess 146, adhered to both the staple cartridge body 80' and the lower distal latch 140 for pulling a hooked proximal end 148 of the lower distal latch 140 down into engagement with a distal side of a lower buttress pad 24' or for pushing the hooked proximal end 148 up and out of engagement. A distal longitudinal slot 150 in the lower buttress pad 24' corresponds to a proximal longitudinal slot 152 formed in the lower distal latch 140 to assist in achieving engagement without contact with the knife or for incomplete severing of the lower buttress pad 24'.

Figure 16:
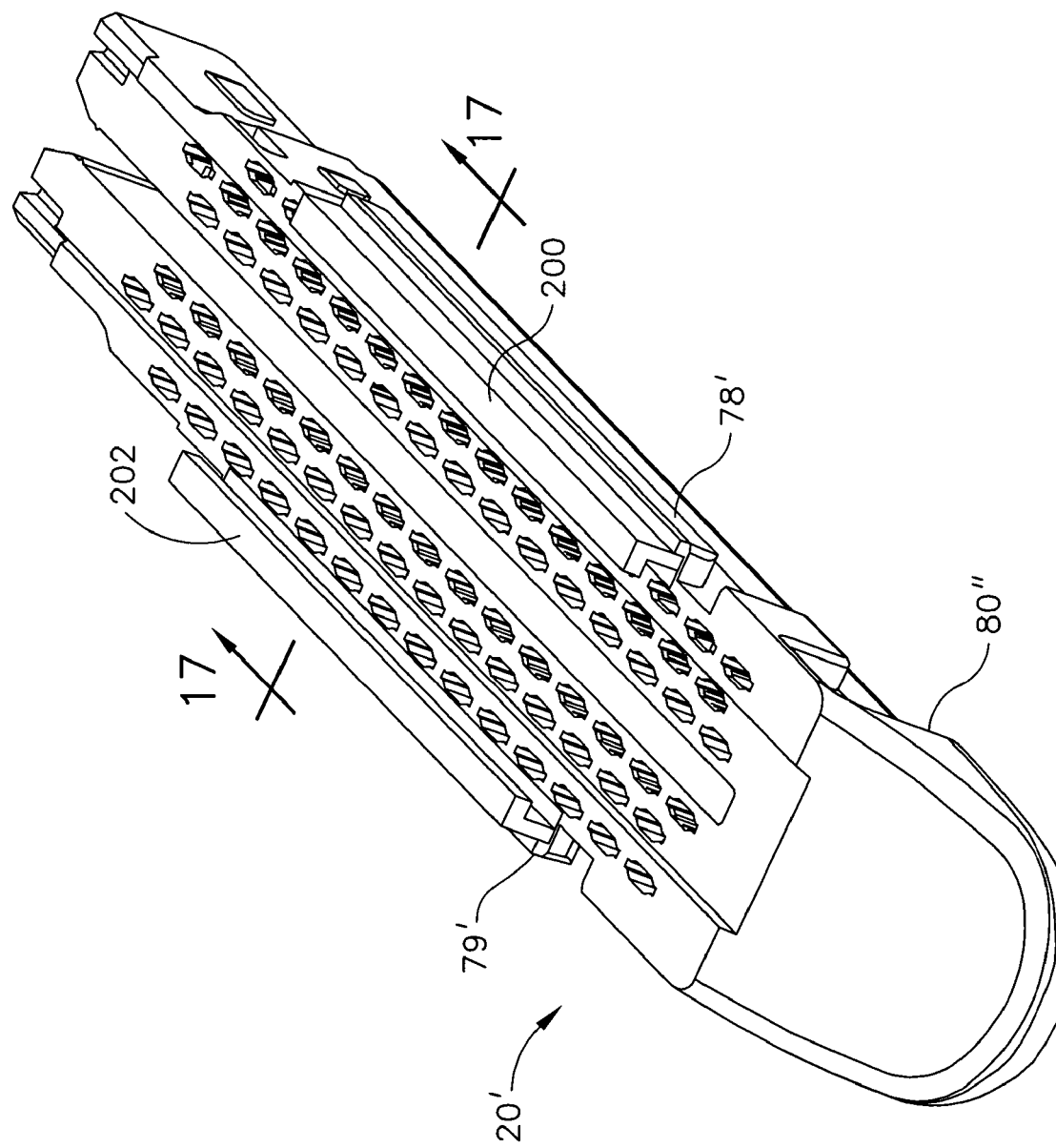
FIG. 16 is a front perspective view of an alternative replaceable staple cartridge with EAP latching channels for the lower jaw for the staple applying assembly of FIG. 2.
Figure 17:
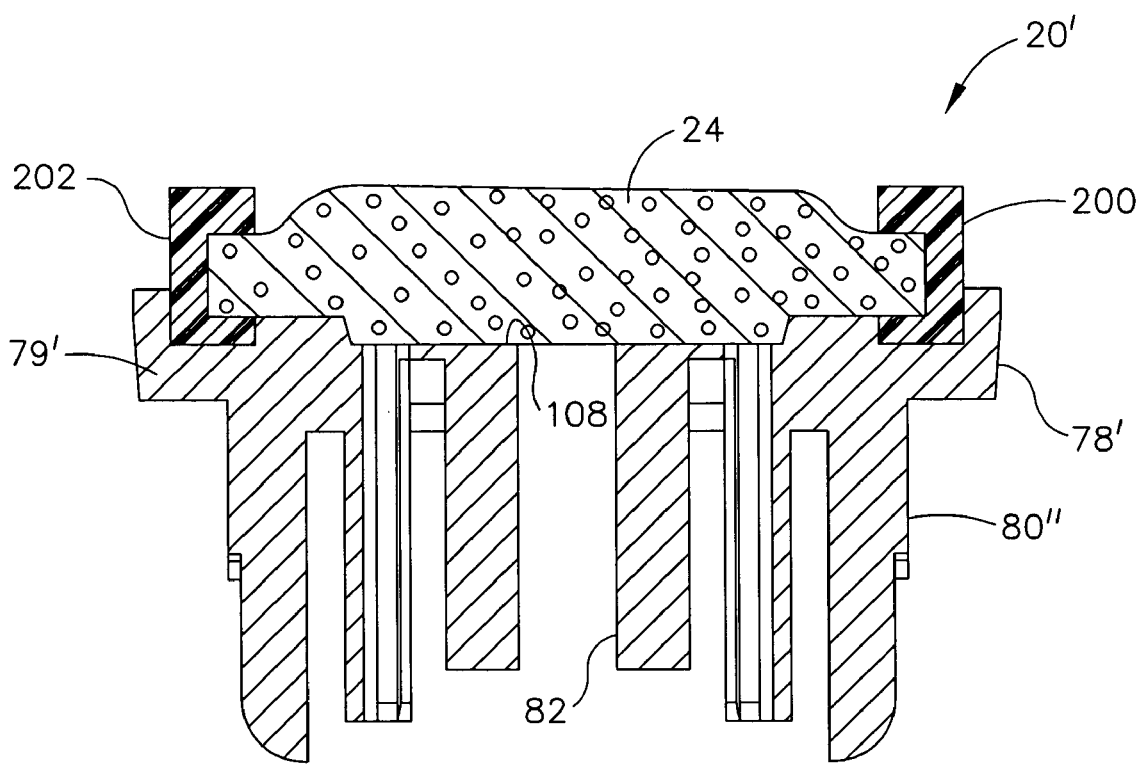
FIG. 17 is a front perspective view of the alternative replaceable staple cartridge of FIG. 16 taken in cross section through lines 17—17 through the deactivated (contracted) EAP latching channel engaged to a buttress pad.
Figure 18:
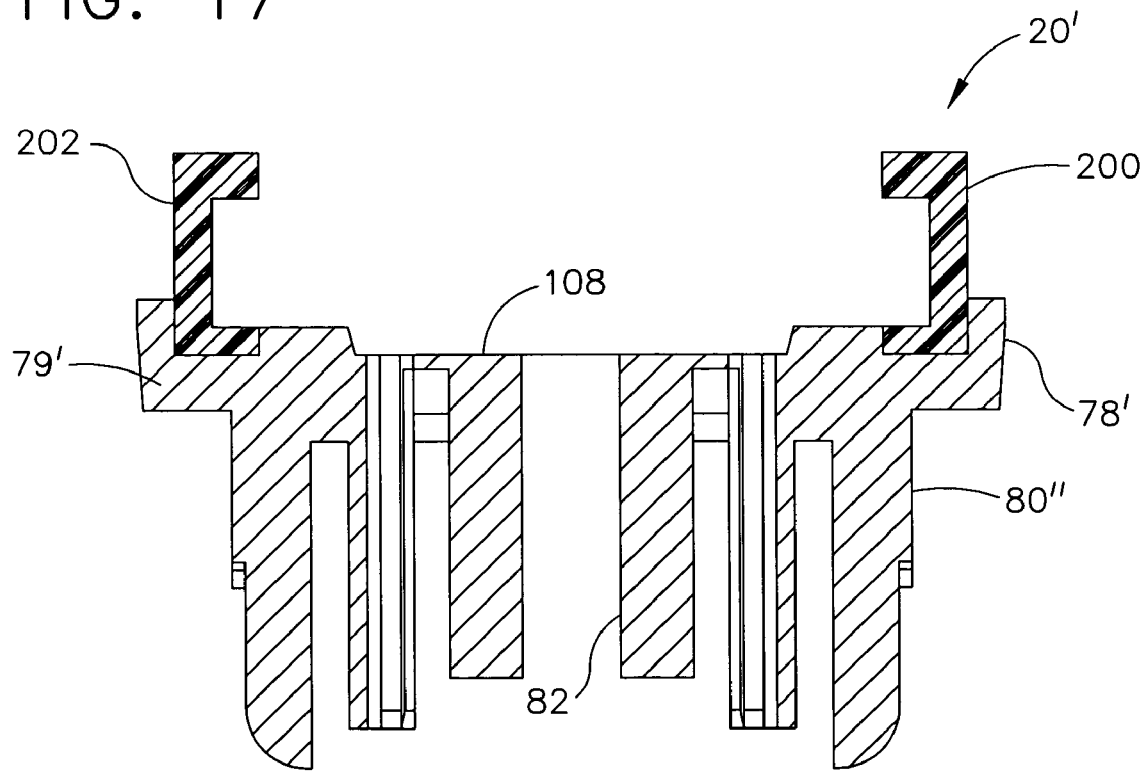
FIG. 18 is a front perspective view of the alternative replaceable staple cartridge of FIG. 16 taken in cross section through lines 17—17 through an activated (expanded) EAP latching channel disengaged from an omitted deployed buttress pad.

In FIGS. 16–18, alternative left and right EAP buttress latches 200, 202 for an electrically actuated buttress deployment mechanism 20' are formed as inwardly open C-channels of EAP material embedded into left and right lateral lips 78', 79' of a staple cartridge body 80" and are configured to vertically contract when deactivated (FIG. 17) to grip a lower buttress pad 24 and to expand when actuated to deploy (FIG. 18).

Figure 19:
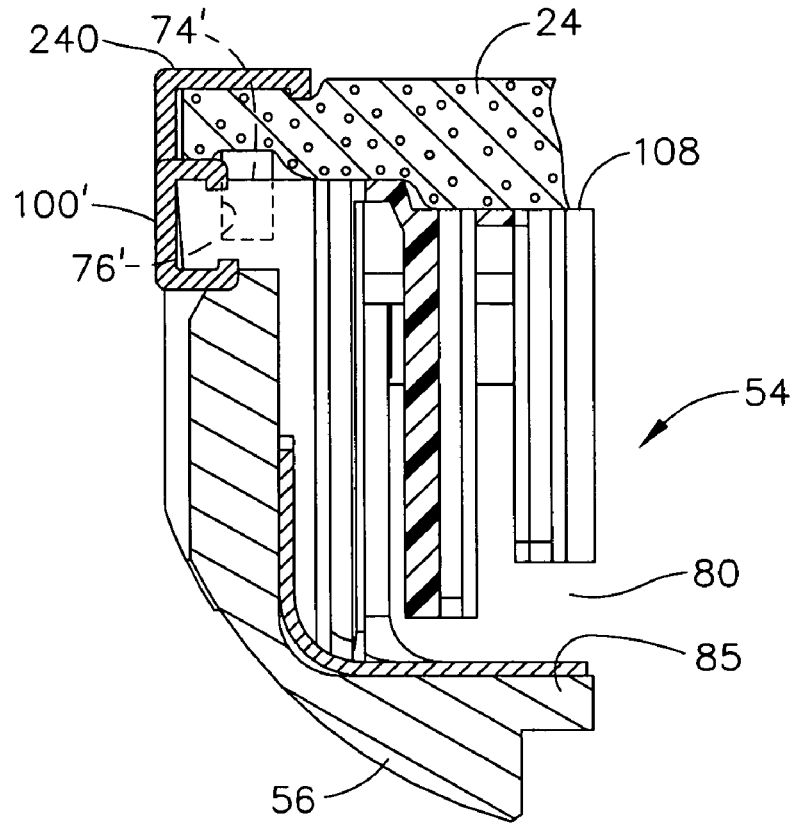
FIG. 19 is a front perspective of a right side of an additional alternative lower jaw for the staple applying assembly of FIG. 2 taken in transverse cross section through a rigid buttress channel with an EAP pinching lock depicted in a deactivated, expanded position locking a buttress pad.
Figure 20:
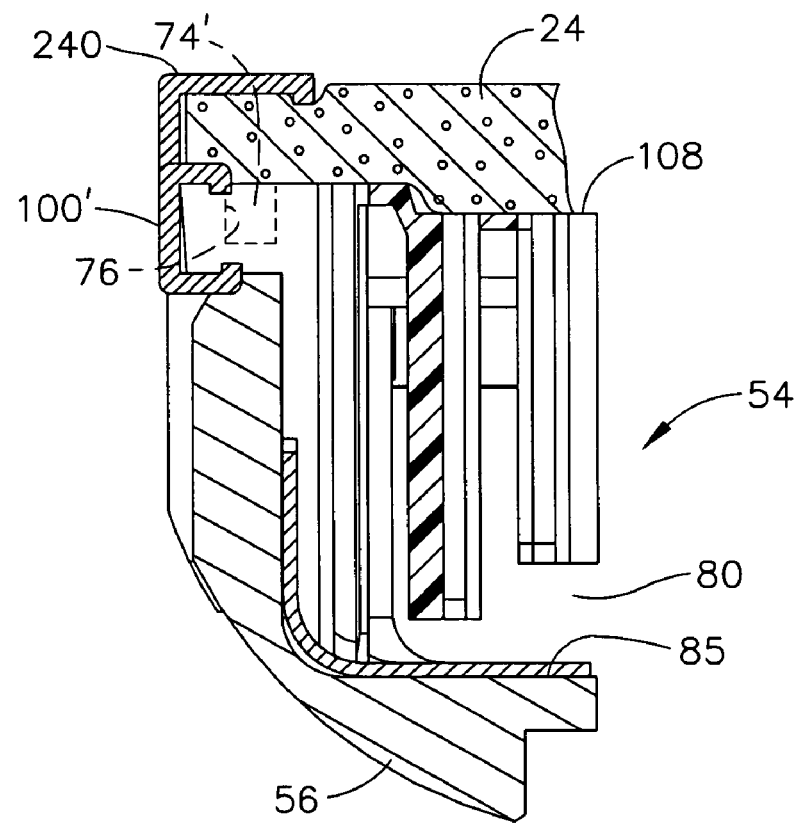
FIG. 20 is a front perspective of the right side of the additional alternative lower jaw of FIG. 19 for the staple applying assembly of FIG. 2 taken in transverse cross section through the rigid buttress channel with the EAP pinching lock depicted in an activated, contracted position unlocked from an omitted deployed buttress pad.

In FIGS. 19–20, an alternative EAP locking actuator 74' is used in the replaceable staple cartridge 54 along with alternative left and right side brackets 100' (the latter depicted) with increased vertical spacing from the top compression surface 108 of the staple cartridge body 80 to loosely hold the lower buttress pad 24. The EAP locking actuator 74' has a vertically expanded locking state (FIG. 19) that pushes the lower buttress pad 24 upwardly into tight engagement in an upper flange 240 of the respective side bracket 100'. The EAP locking actuator 74' has a retracted unlocking state (FIG. 20) that allows deployment. It should be appreciated that recessing the EAP locking actuator 74' into the staple cartridge body 80 provides for a desired amount of extension to deform the buttress pad 24. Alternatively or in addition, an EAP actuator may be placed in an opposing position under the upper flange 240.

Figure 21:
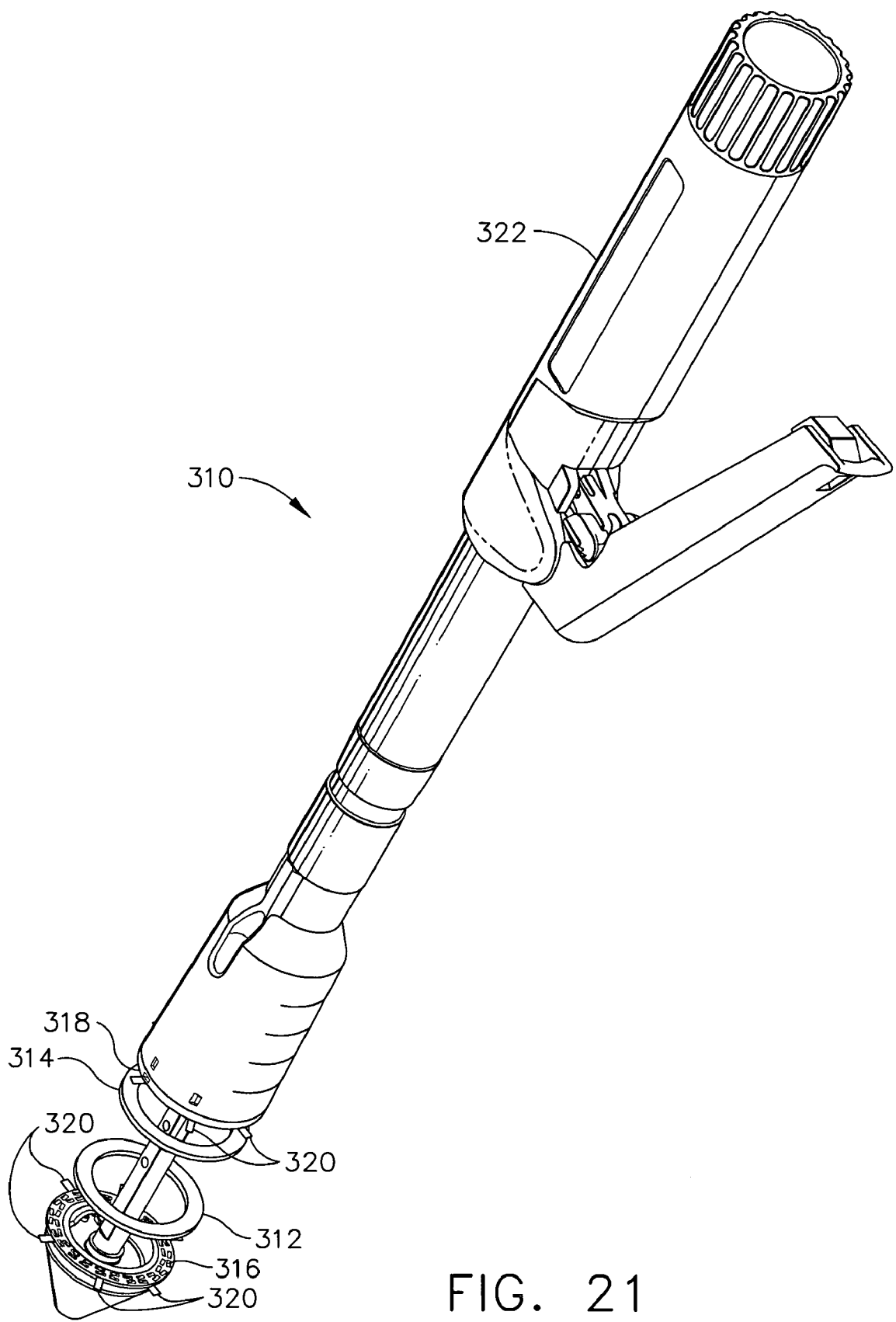
FIG. 21 is a perspective view of a circular surgical stapler with an EAP buttress latching mechanism.

In FIG. 21, a circular stapler instrument 310 has distal and proximal buttress rings 312, 314 depicted as exploded away from distal and proximal circular compression surfaces 316, 318. EAP latches 320 extending inwardly from the compression surfaces 316, 318 and controlled from a handle 322 selectively engage and deploy the buttress rings 312, 314.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a staple applying assembly 16 is depicted in the illustrative version, it should be appreciated that electrically actuated buttress deployment may be advantageously used in fastener instruments that utilize clips, anchors, sutures, etc.

For another example, while a manually operated surgical stapling and severing instrument 10 is depicted for clarity, it should be appreciated that a robotically manipulated and/or controlled fastening device may incorporate electrically actuated buttress retention members consistent with aspects of the invention.

For yet another example, sensing of tissue thickness and/or presence of buttress material may advantageously enable or disable firing to avoid inadvertent firing when buttress material is warranted but not installed or buttress material is installed but not warranted.

For yet a further example, an electrically actuated buttress retention element may comprise a combination of a passive resilient member (e.g., compression spring) that provides a power off retention bias within a buttress gripping channel with an active electrical component. For instance, an EAP fiber actuator passing through the compression spring to a cap may be activated to contract, compressing the compression spring for deployment of a buttress pad.

As yet another example, a staple cartridge may be manufactured with a buttress pad attached to a compression surface by pins, crimped-on clamps, etc., or may be forcibly deployed by an underlying EAP actuator that deforms the buttress pad and/or the attachment to effect separation.

As yet a further example, applications consistent with the present invention may incorporate electrically actuated retention members that are activated to perform engagement to the buttress pad and/or activated to disengage for deployment of the buttress pad. For instance, a retention member may have a loose frictional engagement without power that allows insertion of buttress pads prior to use. Powered activation of a locking EAP actuator thereafter may effectively lock the buttress pad prior to use. Alternatively or in addition to such a locking EAP actuator, activation after stapling of a deployment EAP actuator may effectively reduce engagement or frictional engagement of the buttress pad facilitating deployment.

As yet another additional example, while endosocopic and laparoscopic applications benefit from aspects of the present invention, it should be appreciated that open surgical procedures may also benefit.

What is claimed is:

1. A surgical instrument for fastening buttress material to tissue, comprising;
    an elongate shaft;
    a fastener applying assembly distally attached to the elongate shaft and including opposing tissue compression surfaces;
    an electrically actuated retention member located on said fastener applying assembly and being adapted to hold the buttress material to a selected one of said opposing tissue compression surfaces; and
    control circuitry operably configured to produce a control signal to actuate the electrically actuated retention member to deploy the buttress material.

2. The surgical instrument of claim 1, wherein the electrically actuated retention member further comprises an electroactive polymer.

3. The surgical instrument of claim 1, wherein the electrically actuated retention member further comprises a latch moved by an electroactive polymer actuator.

4. The surgical instrument of claim 1, wherein the electrically actuated retention member further comprises a retention bracket positioned to receive a lateral edge of the buttress material and an electrical actuator having a moving end positioned to selectively enter a channel of the selected opposing tissue compression surfaces.

5. The surgical instrument of claim 4, wherein the electrical actuator is operatively sized to outwardly deform the retention bracket with respect to the selected opposing tissue compression surface to release the lateral edge of buttress material.

6. The surgical instrument of claim 4, wherein the retention member comprises an overlying flange, the electrical actuator positioned on an opposite side of the lateral edge of the buttress material to assert a locking force onto the buttress material.

7. The surgical instrument of claim 1, wherein the electrically actuated retention member comprises an electroactive polymer actuator attached to the selected opposing tissue compression surface operatively configured to change from a compressively engaged state to an expanded disengaged state, a base portion, and a latch portion, wherein in said compressively engaged state of said EAP said base portion extends proximate to a lateral edge of said buttress material engaged on said selected tissue compression surface and in said expanded disengaged state of said EAP said latch portion curves over a surface of a lateral edge of said selected tissue compression surface.

8. The surgical instrument of claim 7, wherein the electroactive polymer actuator is operatively configured to respond to an electrical activation to expand the base portion upwardly and outwardly with respect to the selected opposing tissue compression surface.

9. The surgical instrument of claim 1, wherein the fastener applying assembly comprises a lower jaw containing a staple cartridge and a pivotally attached upper jaw.

10. The surgical instrument of claim 9, wherein the electrically actuated retention member comprises a curved resilient member overlying and attached to a top surface of the upper jaw and extending inwardly curved ends with respect to said upper jaw positioned to hold lateral edges of buttress material positioned on an upper tissue compression surface of the upper jaw, the electrically actuated retention member further comprising a pair of electroactive polymer actuators positioned between the curved resilient member and the top surface of the upper jaw.

11. The surgical instrument of claim 1, wherein the fastener applying assembly comprises a circular staple applying assembly.

12. The surgical instrument of claim 1, further comprising a handle portion operatively configured to distally advance a firing member guided by the elongate shaft to the fastener applying assembly, the control circuitry operatively configured to sense and to respond to firing advance of the firing member to actuate the electrically actuated retention member.

13. The surgical instrument of claim 1, wherein the fastener applying assembly further comprises a clip applying assembly.

14. The surgical instrument of claim 1, wherein the fastener applying assembly further comprises an anchor applying assembly.

15. The surgical instrument of claim 1, wherein the fastener applying assembly further comprises a suture applying assembly.

16. A surgical instrument for fastening buttress material to tissue, comprising:
   an elongate shaft comprising a frame ground guiding a firing member for longitudinal reciprocating motion;
   a handle portion attached to a proximal end of the elongate shaft and operatively configured to longitudinally move the firing member;
   first and second buttress pads;
   a staple applying assembly attached to a distal end of the elongate shaft and comprising opposing tissue compression surfaces operatively configured to respond to distal motion of the firing member towards said distal end of said elongated shaft to form staples between the opposing tissue compression surfaces through the first and second buttress pads and an interposed compressed tissue;
   an electrically actuated retention member selectively positioned between an engaged position holding a selected buttress pad to a selected tissue compression surface; and
   control circuitry operably configured to produce a control signal to actuate the electrically actuated retention member to effect a selected one of retaining and deploying the first and second buttress pads.

17. The surgical instrument of claim 16, wherein the staple applying assembly comprises a lower jaw containing a staple cartridge defining one tissue compression surface and a pivotally attached upper jaw defining the other tissue compression surface.

18. The surgical instrument of claim 16, wherein the staple applying assembly comprises a circular staple applying assembly.

19. The surgical instrument of claim 16, wherein the electrically actuated retention member further comprises an electroactive polymer.

20. A surgical instrument for fastening buttress material to tissue, comprising:
   an elongate shaft;
   a staple applying assembly distally attached to the elongate shaft and including opposing tissue compression surfaces; and
   a means for engaging a buttress pad to each tissue compression surface and to remotely electrically controlling deployment of the buttress pads via electroactive polymer activation after stapling to interposed tissue.

* * * * *